(12) United States Patent
Harti (10) Patent No.: US 11,219,592 B2
(45) Date of Patent: Jan. 11, 2022

(54) USE OF A COMPOSITION FOR THE PIGMENTATION OF HAIR AND HAIRS

(71) Applicant: LEGACY HEALTHCARE LTD., Valleta (MT)

(72) Inventor: Saad Harti, Lutry (CH)

(73) Assignee: Legacy Healthcare (Switzerland) SA, Epalinges (CH)

( * ) Notice: Subject to any disclaimer, the term of this patent is extended or adjusted under 35 U.S.C. 154(b) by 416 days.

(21) Appl. No.: 15/029,891

(22) PCT Filed: Oct. 15, 2014

(86) PCT No.: PCT/EP2014/072160
§ 371 (c)(1),
(2) Date: Apr. 15, 2016

(87) PCT Pub. No.: WO2015/055739
PCT Pub. Date: Apr. 23, 2015

(65) Prior Publication Data
US 2016/0263012 A1    Sep. 15, 2016

(30) Foreign Application Priority Data

Oct. 16, 2013 (EP) .................................... 13188942

(51) Int. Cl.
| | | |
|---|---|---|
| *A61Q 5/10* | (2006.01) | |
| *A61K 36/8962* | (2006.01) | |
| *A61K 36/185* | (2006.01) | |
| *A61K 36/752* | (2006.01) | |
| *A61K 36/77* | (2006.01) | |
| *A61K 36/88* | (2006.01) | |
| *A61K 8/9789* | (2017.01) | |
| *A61K 8/9794* | (2017.01) | |

(52) U.S. Cl.
CPC .......... *A61K 8/9789* (2017.08); *A61K 8/9794* (2017.08); *A61K 36/185* (2013.01); *A61K 36/752* (2013.01); *A61K 36/77* (2013.01); *A61K 36/88* (2013.01); *A61K 36/8962* (2013.01); *A61Q 5/10* (2013.01); *A61K 2236/33* (2013.01); *A61K 2800/5922* (2013.01)

(58) Field of Classification Search
CPC .. A61K 36/752; A61K 36/8962; A61K 36/88; A61K 36/77; A61K 36/185
See application file for complete search history.

(56) References Cited

U.S. PATENT DOCUMENTS

| | | | |
|---|---|---|---|
| 5,773,241 A | 6/1998 | Ericsson | |
| 6,582,702 B2 | 6/2003 | Rigby | |
| 7,157,109 B2 | 1/2007 | Kipfer | |
| 8,088,431 B2 | 1/2012 | Ward et al. | |
| 8,361,522 B2 | 1/2013 | Ulmann et al. | |
| 8,652,543 B2 | 2/2014 | Ulmann et al. | |
| 2003/0077336 A1 | 4/2003 | Maffetone | |
| 2004/0076614 A1 | 4/2004 | Schur | |
| 2006/0018867 A1 | 1/2006 | Kawasaki et al. | |
| 2008/0305096 A1 | 12/2008 | Verdegem et al. | |
| 2010/0104671 A1* | 4/2010 | Ulmann .................... | A61K 8/27 424/736 |
| 2010/0154144 A1* | 6/2010 | Guerin ...................... | A61K 8/19 8/424 |
| 2012/0064174 A1 | 3/2012 | Harti et al. | |
| 2013/0108719 A1 | 5/2013 | Ulmann et al. | |
| 2013/0323334 A1 | 12/2013 | Harti | |
| 2016/0256512 A1 | 9/2016 | Harti et al. | |
| 2019/0314441 A1 | 10/2019 | Harti et al. | |

FOREIGN PATENT DOCUMENTS

| | | | |
|---|---|---|---|
| CH | 682217 A5 | 8/1993 | |
| DE | 2844614 A1 | 5/1980 | |
| DE | 19533777 A1 | 3/1997 | |
| DE | 202004012348 U1 | 10/2004 | |
| DE | 102004011968 A1 | 9/2005 | |
| DE | 102005010142 A1 | 11/2005 | |
| EP | 0467660 A2 | 1/1992 | |
| FR | 2706771 A1 | 12/1994 | |
| FR | 2865132 A1 | 7/2005 | |
| FR | 2877219 A1 | 5/2006 | |
| FR | 2877576 A1 | 5/2006 | |
| JP | 08268863 A | * | 10/1996 |
| JP | H09194334 A | 7/1997 | |
| JP | 09249578 A | * | 9/1997 |
| JP | 2000044439 A | 2/2000 | |
| JP | 2000247830 A | 9/2000 | |
| JP | 2003201229 A | 7/2003 | |
| JP | 2006104098 A | 4/2006 | |
| JP | 2006342120 A | 12/2006 | |
| KR | 20070022018 A | 2/2007 | |

(Continued)

OTHER PUBLICATIONS

"Good Housekeeping". vol. 6. Nov. 12, 1887-Apr. 28, 1888. Clark W. Bryan and Co: Massachusetts, p. 191. (Year: 1888).*
Abdullah, Fadwah et al., "Alopecia: Botanical Approaches in Review." Journal of Drugs in Dermatology, vol. 9, No. 5, pp. 537-541, May 2010.
Aktas, Aynur et al., "Symptom clusters: myth or reality?" Palliative Medicine, vol. 24, No. 4, pp. 373-385, 2010.
Bower, Julienne E. et al., "Inflammation and cancer-related fatigue: Mechanisms, contributing factors, and treatment implications." Brain, Behavior, and Immunity, vol. 30, No. 0, pp. S48-S57, Mar. 2013.
Bower, Julienne E., "Cancer-related fatigue: Links with inflammation in cancer patients and survivors." Brain, Behavior, and Immunity, vol. 21, pp. 863-871, 2007.
Bower, Julienne E., "Cancer-related fatigue: Mechanisms, risk factors, and treatments." Nature Reviews Clinical Oncology, vol. 11, No. 10, pp. 597-609, 2014.

(Continued)

*Primary Examiner* — Amy L Clark
(74) *Attorney, Agent, or Firm* — Harness, Dickey & Pierce, PLC (57) ABSTRACT

A topical composition including an extract of *Allium* species, an extract of *Citrus* species, an extract of *Paullinia* species and an extract of *Theobroma* species is used for improving and/or increasing and/or stimulating and/or promoting and/or inducing the pigmentation of hair and/or hairs.

9 Claims, 4 Drawing Sheets

(56) References Cited

FOREIGN PATENT DOCUMENTS

| KR | 100811298 B1 | 3/2008 | | |
|---|---|---|---|---|
| WO | WO-2005120452 A1 | 12/2005 | | |
| WO | WO-2008/015341 A2 | 2/2008 | | |
| WO | WO-2008015341 A2 * | 2/2008 | ............... | A61K 8/97 |
| WO | WO-2008113912 A2 | 9/2008 | | |
| WO | WO-2012113820 A1 | 8/2012 | | |
| WO | WO-2012/140013 A2 | 10/2012 | | |
| WO | WO-2012140013 A2 * | 10/2012 | ............... | A61K 8/97 |
| WO | WO-2013020719 A2 | 2/2013 | | |

OTHER PUBLICATIONS

Carroll, Jennifer K. et al., "Pharmacologic Treatment of Cancer-Related Fatigue." The Oncologist, vol. 12 (Supplement 1), pp. 43-51, 2007.

Fan, G. et al., "Symptom clusters in cancer patients: a review of the literature." Current Oncology, vol. 14, No. 5, pp. 173-179, 2007.

Fiorentino, Lavinia et al., "The Symptom Cluster of Sleep, Fatigue and Depressive Symptoms in Breast Cancer Patients: Severity of the Problem and Treatment Options." Drug Discovery Today: Disease Models, vol. 8, No. 4, pp. 167-173, 2011.

Paus, R. et al., "Telogen skin contains an inhibitor of hair growth." British Journal of Dermatology, vol. 122, pp. 777-784, 1990.

Puri, Neerja et al., "A Study of Nail Changes in Various Dermatosis in Punjab, India." Our Dermatology Online, vol. 3, No. 3, pp. 164-170, 2012.

Tavio, Marcello et al., "Cancer-related fatigue (Review)." International Journal of Oncology, vol. 21, pp. 1093-1099, 2002.

Tzia, C. et al., Extraction Optimization in Food Engineering, National Technical University of Athens, p. 194, 2005.

Wang, Xin Shelley et al., "Cancer-Related and Treatment-Related Fatigue." Gynecologic Oncology, vol. 136, No. 3, pp. 446-452, Mar. 2015.

Wang, Xin Shelley, "Pathophysiology of Cancer-Related Fatigue." Clinical Journal of Oncology Nursing, vol. 12, No. 5 (Supplemental), pp. 11-20, Oct. 2008.

Chen, Daniel S. et al., "Oncology Meets Immunology: The Cancer-Immunity Cycle." Immunity, vol. 39, No. 1, pp. 1-10, Jul. 2013.

Chu, Heuy-Ling, "Effects of Selected Organo-sulfur Compounds on Melanin Formation." Journal of Agricultural and Food Chemistry, vol. 57, No. 15, pp. 7072-7077, 2009.

Macciò, Antonio et al., "Blocking inflammation to improve immunotherapy of advanced cancer." Immunology, vol. 159, No. 4, pp. 357-364, Apr. 2020.

Qu, Xinglong et al., "Immunological Approaches Towards Cancer and Inflammation: A Cross Talk." Frontiers in Immunology, vol. 9, No. 563, pp. 1-19, Mar. 2018.

* cited by examiner

USE OF A COMPOSITION FOR THE PIGMENTATION OF HAIR AND HAIRS

CROSS-REFERENCE TO RELATED APPLICATIONS

This application is a National Phase Entry of International Patent Application No. PCT/EP2014/072160, filed on Oct. 15, 2014, which claims priority to European Patent Application Serial No. 13188942.0, filed on Oct. 16, 2013, both of which are incorporated by reference herein.

TECHNICAL FIELD

The invention relates to the use of a composition comprising an extract of *Allium* species, an extract of *Citrus* species, an extract of *Paullinia* species and an extract of *Theobroma* species for improving and/or increasing and/or stimulating and/or promoting and/or inducing the pigmentation of hair and/or hairs.

BACKGROUND

The color of hair is largely determined by melanocytes, which produce melanin as the main contributor to pigmentation. Melanocytes are proliferated and differentiated from melanocyte stem cells (McSCs).

Hair graying is a visible sign of senescence and aging. Hair turns from its original pigmentation to white as melanin production reduces. The biological process of hair graying is attributed to the depletion of the hair pigment producing melanocytes. Production of melanocytes and production of keratinocytes happen both during the growth phase of the hair cycle, known as the anagen phase.

In many populations, people want to maintain a constant coloration of the hair. However, for many people, hair and/or hairs become gray or white after a certain age which can vary from one person to another. This phenomenon is called canitie and occurs during the life of a person. Nevertheless, people generally want to have a younger appearance and in a cosmetic objective, people usually try to avoid this phenomenon, in particular when said phenomenon occurs at an early age.

Such a progressive hair graying process will lead to fully white hair. Both women and men commonly apply chemical dyes and colorant on graying hair in order to hide this sign of aging.

Nevertheless, chemicals dyes and colorants present some drawbacks. Since the artificial pigments vanish and/or since the hair grows, the hair shows its original gray pattern only after few weeks after application, forcing users to repeat the dying process indefinitely. In addition to hair quality regression, the safety issue of long term use of dyes remains a concern. Chemical dies and colorants cover the hair with a color which does not always look natural and is not necessarily well suited to the person's skin tone.

Document WO 2008/113912 describes compositions comprising an extract of *Allium* species, an extract of *Citrus* species, an extract of *Paullinia* species and an extract of *Theobroma* species having effects on excessive hair loss and insufficient hair growth. Nevertheless, said document is silent about the hair pigmentation properties of these compositions.

Currently, there does not exist any satisfying solution to the problem of preventing the hair from turning gray or recovering the hair's natural and original colour after it has turned gray. The author of the present invention surprisingly found that a composition comprising an extract of *Allium* species, an extract of *Citrus* species, an extract of *Paullinia* species and an extract of *Theobroma* species can improve and/or increase and/or stimulate and/or promote and/or induce the pigmentation of hair and hairs.

SUMMARY

The present invention relates to the use of a composition comprising an extract of *Allium* species, an extract of *Citrus* species, an extract of *Paullinia* species and an extract of *Theobroma* species for improving and/or increasing and/or stimulating and/or promoting and/or inducing the pigmentation of hair and/or hairs. According to an embodiment, the composition comprises an aqueous alcoholic extract of *Allium* species, an aqueous alcoholic extract of *Citrus* species, an aqueous alcoholic extract of *Paullinia* species and an aqueous alcoholic extract of *Theobroma* species. According to an embodiment, the composition comprises an extract of *Allium cepa*, an extract of *Citrus lemon*, an extract of *Paullinia* cupana and an extract of *Theobroma cacao*.

Preferably, the composition comprises:
  from 0.1 to 5% by dry weight of an extract of *Allium* species,
  from 0.1 to 5% by dry weight of an extract of *Citrus* species,
  from 0.05 to 2.5% by dry weight of an extract of *Paullinia* species, and
  from 0.05 to 2.5% by dry weight of an extract of *Theobroma* species, based on the total weight of the composition.

According to an embodiment, the concentration of the composition is from 1 to 30% dry weight of active principles as compared to the volume of the composition. According to an embodiment, the composition is used for pigmenting hair and/or hairs. According to an embodiment, the composition is used for preventing and/or reducing the depigmentation of hair and/or hairs. According to an embodiment, the composition is used for allowing white or grey hair to grow with its natural colour.

The present invention also concerns a cosmetic method for improving and/or increasing and/or stimulating and/or promoting and/or inducing the pigmentation of hair and/or hairs, comprising the administration of a composition comprising an extract of *Allium* species, an extract of *Citrus* species, an extract of *Paullinia* species and an extract of *Theobroma* species. Preferably, the composition is as defined in the present invention. According to an embodiment, the administration is by topical route. Preferably, the concentration of the composition is from 1 to 30% dry weight of active principles as compared to the volume of the composition, and the topical administration comprises the application of 10 µL to 10 mL of the composition onto the scalp or the skin.

The present invention further concerns a composition comprising as active principles an extract of *Allium* species, an extract of *Citrus* species, an extract of *Paullinia* species and an extract of *Theobroma* species for the treatment of canitie. The composition according to the present invention has the ability to prevent pigmented hair to turn into grey or white hair. The composition according to the present invention has the ability to allow white/grey hair to grow again in its original color. The advantages are: the composition is not toxic and can be used safely in a repeated/chronic manner for as long as it is desired, it provides a natural appearance, recoloring of whitened or greyed hair is progressive, the color is identical or close to the original color of the individual's hair. Further features and advantages of the invention will appear from the following description of embodiments of the invention, given as non-limiting examples, with reference to the accompanying drawings listed hereunder.

DETAILED DESCRIPTION

The present invention relates to the use, in particular cosmetic use and/or non-therapeutic use, of a composition comprising an extract of *Allium* species, an extract of *Citrus* species, an extract of *Paullinia* species and an extract of *Theobroma* species for improving and/or increasing and/or stimulating and/or promoting and/or inducing the pigmentation of hair and/or hairs. The composition may also be used to prevent and/or reduce the depigmentation of hair and/or hairs. The expression "hairs" includes beard hair, whiskers, eyelashes, eyebrows, and other body hairs.

The term extract of Mum species or aqueous-alcoholic extract of *Allium* species refers particularly to aqueous-alcoholic extracts and native extracts obtained from all species of the genus *Allium* (family Liliaceae) and especially *Allium cepa*. Extract of *Citrus* species or aqueous-alcoholic extract of *Citrus* species refers particularly to aqueous-alcoholic extracts and native extracts obtained from all species of the genus *Citrus* (family Rutaceae) and especially *Citrus lemon*. Extract (atomised or not) of *Paullinia* species or aqueous-alcoholic extract (atomised or not) of *Paullinia* species refers particularly to aqueous-alcoholic extracts and native extracts obtained from all species of the genus *Paullinia* (family Sapindaceae) and especially *Paullinia cupana*. Extract (atomised or not) of *Theobroma* species or aqueous-alcoholic extract (atomised or not) of *Theobroma* species refers particularly to aqueous-alcoholic extracts and native extracts obtained from all species of the genus *Theobroma* (family Malvaceae) and especially *Theobroma cacao*.

Preferably, the composition comprises an aqueous alcoholic extract of *Allium* species, an aqueous alcoholic extract of *Citrus* species, an aqueous alcoholic extract of *Paullinia* species and an aqueous alcoholic extract of *Theobroma* species. Preferably, the composition comprises an extract of *Allium cepa*, an extract of *Citrus lemon*, an extract of *Paullinia cupana* and an extract of *Theobroma cacao*. The composition according to the present invention may be prepared starting from a concentrate of active principles comprising an extract of *Allium* species, an extract of *Citrus* species, an extract of *Paullinia* species and an extract of *Theobroma* species.

Preferably, the concentrate comprises:
from 65 to 93% by dry weight of an extract of *Allium* species,
from 5 to 33% by dry weight of an extract of *Citrus* species,
from 0.25 to 2.5% by dry weight of an extract of *Paullinia* species, and
from 0.25 to 2.5% by dry weight of an extract of *Theobroma cacao*,
based on the total weight of the concentrate.

Preferably, the concentrate consists essentially of:
from 65 to 93% by dry weight of an extract of *Allium* species,
from 5 to 33% by dry weight of an extract of *Citrus* species,
from 0.25 to 2.5% by dry weight of an extract of *Paullinia* species, and
from 0.25 to 2.5% by dry weight of an extract of *Theobroma cacao*,
based on the total weight of the concentrate.

According to an embodiment, the composition comprises:
from 0.1 to 5% by dry weight, preferably from 0.3 to 4% by dry weight, more preferably from 0.5 to 3% by dry weight of an extract of *Allium* species,
from 0.1 to 5% by dry weight, preferably from 0.2 to 4% by dry weight, more preferably from 0.3 to 3% by dry weight of an extract of *Citrus* species,
from 0.05 to 2.5% by dry weight, preferably from 0.07 to 1.5% by dry weight, more preferably from 0.09 to 1% by dry weight of an extract of *Paullinia* species, and
from 0.05 to 2.5% by dry weight, preferably from 0.07 to 2% by dry weight, more preferably from 0.09 to 1.5% by dry weight of an extract of *Theobroma* species,
based on the total weight of the composition.

According to an embodiment, the active principles of the composition of the invention comprise an extract of *Allium* species, an extract of *Citrus* species, an extract of *Paullinia* species and an extract of *Theobroma* species. Preferably, the active principles of the composition of the invention consist essentially in an extract of *Allium* species, an extract of *Citrus* species, an extract of *Paullinia* species and an extract of *Theobroma* species. Preferably, the concentrate represents from 1 to 30% by weight, preferably from 1.5 to 15% by weight, more preferably from 2 to 10% by weight in dry weight as compared to the volume of the composition.

The composition may be prepared by dilution of the concentrate of active principles. The dilution may be performed in one or more solvents and/or in one or more excipients and/or in one or more other additives.

According to an embodiment, the composition further comprises excipients, said excipients being dermatologically acceptable. Preferably, excipients are chosen from talc, gum arabic, lactose, starch, magnesium stearate, cocoa butter, fatty substances of animal or vegetable origin, paraffin derivatives, glycols, various wetting agents, dispersants or emulsifiers and preservatives. According to an embodiment of the invention, the composition further comprises other additives such as, for example, diluents, disintegrators, binders, lubricants, wetting agents, stabilizers, emulsifiers, preservatives, sweeteners, colorants, flavours or fragrances, thickeners and buffering agents, and also solvents or solubilizers, retarders, osmotic pressure-modifying salts, coating materials or antioxidants. Preferably, the composition further comprises at least one agent for promoting penetration and diffusion in the cutaneous structures in question, such as agents commonly used in the field of cosmetology, for example glycerol, propylene glycol, oleic acid or essential oils, in particular menthol and eucalyptol. The composition according to the present invention may be prepared according to the method described in document WO 2008/113912.

The composition may be administered by topical route and/or by oral route. Preferably, the compositions according to the present invention are intended for topical applications, wherein the compositions are applied on the scalp and/or on the skin. The composition according to the present invention may be in a liquid or a solid form. These compositions can be in the form of a lotion, a spray, a foam, a solution, a powder, a pomade, a milk, an emulsion, a cream or a hydrogel. The expression "topical applications" includes both conventional topical route and non-conventional topical route. Among non-conventional topical route, mention may be made of cell suspension solution, cell-carrier (also called cell-spray) or adjuvant potentiator in cell therapy.

The topical composition can be prepared by diluting the active principles into a cosmetically acceptable carrier. Preferably, the topical composition is in the form of a solution or a lotion comprising from 1 to 30% by weight of dry matter, preferably from 1.5 to 15% by weight of dry matter, more preferably from 2 to 10% by weight of dry matter of the four active principles as defined above, as compared to the volume of the composition. Advantageously, the composition is under the form of an aqueous alcoholic solution or a lotion comprising from 1 to 30% by weight of dry matter, preferably from 1.5 to 15% by weight of dry matter, more preferably from 2 to 10% by weight of dry matter of the four active principles as defined above, as compared to the volume of the composition.

The compositions may also be orally administered, for example in the form of tablets, coated tablets, film-coated forms, granules, capsules, soft capsules, microcapsules, solutions, syrups, emulsions, suspensions or aerosol mixtures. According to an embodiment, the compositions are administered as food supplements in the form of granules, flexible capsules or drinks, depending on the final form required. Instead of using the four active principles in the form of an aqueous alcoholic solution, the four active principles may also be used in a dry form obtained from the solution, for example by atomization, freeze-drying, concentration or secondary extraction of the aqueous-alcoholic solution with super-critical $CO_2$.

Suitable carriers for soft gelatine capsules comprise for example, fats, waxes, semi-solid or liquid polyols, natural or modified oils, etc. Suitable vehicles for the preparation of solutions, for example, injectable solutions, emulsions or syrups, comprise, for example, water, alcohols, glycerol, polyols, sucrose, invert sugars, glucose, vegetable oils, etc. Suitable carriers for microcapsules comprise, for example, copolymers of glyoxylic acid and lactic acid.

The composition may be administered daily for several months. The administration mode may be varied according to the concentration of active principles in the composition. According to a specific embodiment, the composition is administered one to three times per day during at least one week, preferably at least one month, more preferably at least three months, even more preferably at least six months.

The composition is preferably for administration to humans. The composition according to the present invention may be used to pigment hair or hairs, in particular to pigment depigmented hair or hairs. It can be used to pigment partially depigmented hair(s) or totally depigmented hair(s).

Applying the composition according to the present invention on the scalp turns progressively a white appearing scalp into a natural color appearing scalp, for example into a dark appearing scalp. One significant advantage of the invention is that the hair color which appears as a consequence of the treatment is the individual's original pigmentation color. For this reason the treatment according to the invention is more satisfying than the artificial appearance generally provided by colorants or dies.

The composition according to the present invention may be used in the correction of hair pigmentation disorders originating from a functional alteration of melanocytes. The present invention also relates to a cosmetic method for improving and/or increasing and/or stimulating and/or promoting and/or inducing the pigmentation of hair and/or hairs, comprising the administration of a composition comprising an extract of *Allium* species, an extract of *Citrus* species, an extract of *Paullinia* species and an extract of *Theobroma* species.

The composition may be administered by topical route and/or by oral route, preferably the composition is topically administered. Preferably, the composition is topically applied on the scalp of the human. Preferably, when the composition is in a liquid form, the topical administration comprises the application of 10 µL to 10 mL of the composition according to the invention onto the scalp of the humans. This application can be operated from 1 to 5 times per day, preferably, from 1 to 3 times per day.

For oral administration, the daily dose generally varies between 0.05 and 10 mg of active principle (dry matter)/kg of individual, preferably from 0.1 to 8 mg/kg, particularly from 0.1 to 6 mg/kg. For example, a daily dose varying from 5 to 500 mg would be appropriate for an adult.

The present invention further relates to a composition comprising an extract of *Allium* species, an extract of *Citrus* species, an extract of *Paullinia* species and an extract of *Theobroma* species for the treatment of canitie. The invention has been described with reference to preferred embodiments. However, many variations are possible within the scope of the invention.

EXAMPLES

In the examples, the composition is prepared starting from a concentrate A comprising the four active principles:
- 87.04% by dry weight of an aqueous-alcoholic extract of *Allium* cepa,
- 11.96% by dry weight of an aqueous-alcoholic extract of *Citrus lemon*,
- 0.50% by dry weight of an atomised aqueous-alcoholic extract of *Paullinia cupana*,
- 0.50% by dry weight of an atomised aqueous-alcoholic extract of *Theobroma cacao*,
- based on the total weight of the concentrate, was prepared according to the following process.

The aqueous-alcoholic extract of *Allium cepa* was prepared by picking, cleaning and milling the *Allium*, macerating in 96° alcohol for 48 hours in the cold, filtering through a 0.22-micron filter, collecting the alcoholic filtrate and adjusting to 30° alcohol. The aqueous-alcoholic extract of *Citrus lemon* was prepared by picking, cleaning and milling the *Citrus*, macerating in 96° alcohol for 48 hours in the cold, filtering through a 0.22-micron filter, collecting the alcoholic filtrate and adjusting to 30° alcohol. A master solution containing the aqueous-alcoholic extracts of *Allium* and *Citrus* was prepared by simple mixing, then the atomised aqueous-alcoholic extracts of *Paullinia cupana* and *Theobroma cacao* were added to this master solution to give the required concentrate A.

The concentrate A was then conditioned in the form of a lotion, by mixing about 20 mL of the concentrate comprising the four active principles and completing until 100 mL with the following excipients:

| | |
|---|---|
| Glycerin | 2 g |
| Betafin | 2 g |
| Sodium chloride | 0.9 g |
| Fragrance | 0.15 to 3 g depending on the fragrance | in order to obtain a composition according to the present invention.

The composition obtained, also named the lotion, comprises about 2.35% by dry weight of an extract of *Allium cepa*, about 0.32% by dry weight of an extract of *Citrus lemon*, about 0.10% by dry weight of an extract of *Paullinia cupana* and about 0.10% by dry weight of an extract of *Theobroma cacao*, based on the total weight of the lotion.

Example 1

Figure 1A:
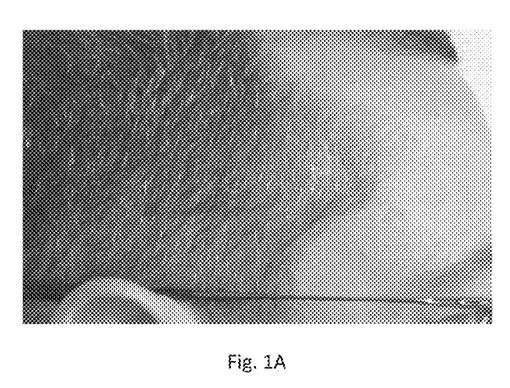
FIG. 1 shows the appearance of two different parts of a scalp, the composition according to the invention was applied onto only one part of the scalp.
Figure 1B:
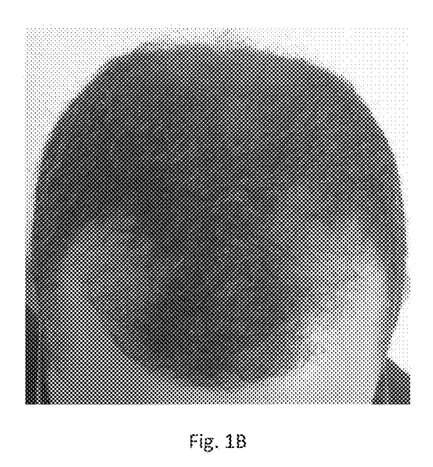

In said example, the composition was applied on the top of the scalp (vertex) whereas the composition was not applied on the temples. The subject is a 42 years old man with black hair as original hair color. An average of 1 mL of the topical lotion was applied twice daily for two years. As illustrated in FIG. 1, we observe that the temple turned to grey appearance (FIG. 1A), whereas the top of the scalp (vertex) remained of dark appearance (FIG. 1B).

Example 2

In said example, the composition was applied on the scalp of a 30 years old man for 9 months twice daily. The subject is a 30 years old man having white or grey hair, but originally having black hair as natural hair color. An average of 1 mL of the topical lotion was applied twice daily for 9 months on the scalp.

As the subject started applying the lotion twice daily, he noticed that the white hair base was becoming black as the hair was growing from the scalp. Since the hair grows by half a centimetre on average every month, the phenomenon was rapidly noticeable. After application of the composition according to the present invention on the scalp, grey hair of the subject grew pigmented, i.e. with natural color of the subject.

Figure 2:
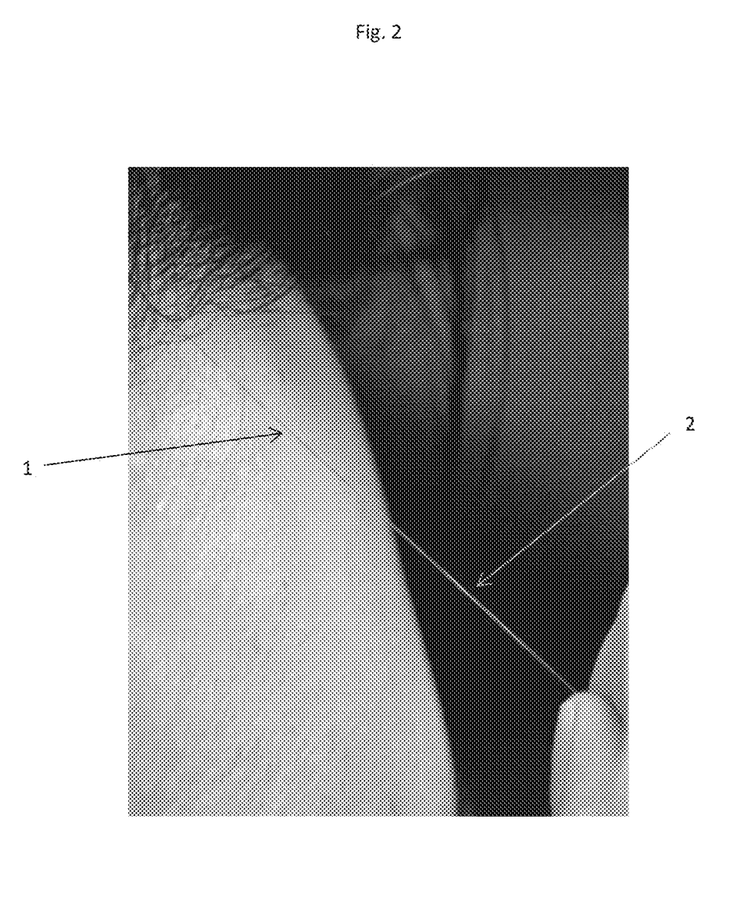
FIG. 2 shows the pigmented growing of white hair after application of the composition according to the invention.

FIG. 2 illustrates the above-mentioned case of a hair, wherein the hair root 1 is black, corresponding to the natural hair color of the subject and the hair end 2 is white. Indeed, we observe in FIG. 2 that after application of the composition of the invention, the hair grows with its natural color (hair root 1 of FIG. 2).

Example 3

Figures 3, 3A:
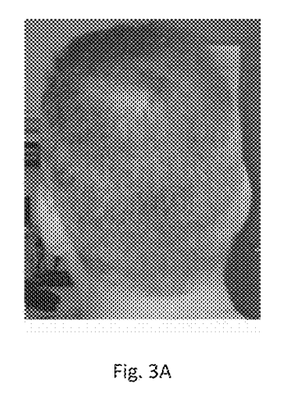
FIG. 3 shows the appearance of a scalp before and after application of the composition according to the invention.

In said example, the composition was applied on the scalp of a 63 years old man for 3 months. The subject is a 63 years old man having black hair as natural color and presenting grey hair since several years. FIG. 3A is a photography of the hair of the subject before application of the composition, where two-third of the scalp looks white. An average of 1 mL of the topical lotion was applied twice daily for 3 months on the scalp.

Figures 3, 3B:
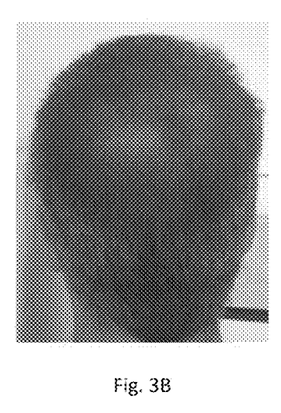

FIG. 3B is a photograph of the hair of the subject after 3 months of application of the composition according to the present invention, where two-third of the scalp looks now dark. We observe in FIG. 3B that after 3 months of application, during which the hair growth is about 1.5 cm, and after several haircuts (to keep an about constant hair length), the scalp is darker than before application.

Example 4

Figures 4, 4A:
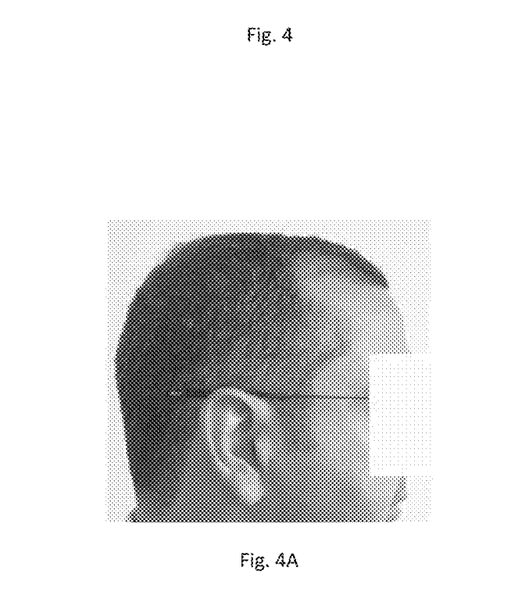
FIG. 4 shows the appearance of a scalp before and after application of the composition according to the invention.

In said example, the subject is a 42 years old man having black natural hair and presenting hair graying. As illustrated in FIG. 4A, before the treatment 75% of the surface of the temple of the subject looks more white than black. An average of 1 mL of the topical lotion was applied twice daily for 3 weeks on the temples.

Figure 4B:
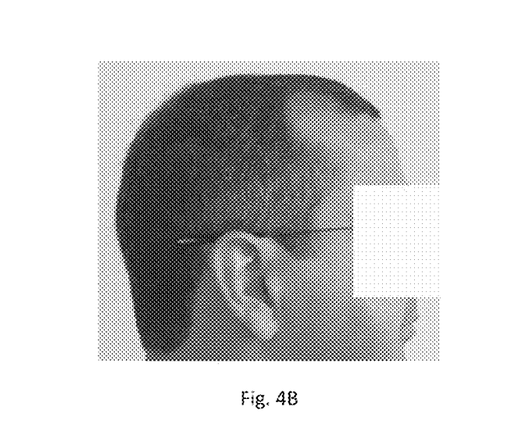

After 3 weeks of application, we observe in FIG. 4B than only 25% of temple surface still looks white, and the rest is darker than in FIG. 4A. Indeed, as illustrated in FIG. 4B, the temple of the subject after application of the composition according to the present invention looks more black than white. As mentioned above, applying the composition enables the hair to grow with its original natural colour. Thus, the hair roots grow re-pigmented, which provides a visual effect of overall darkening, as illustrated in FIGS. 3B and 4B.

The invention claimed is:

1. A method for improving, increasing, stimulating, promoting and/or inducing the pigmentation of hair of a subject in need thereof, wherein said subject has white or grey hair, the method comprising:
   administering an effective amount of a composition to said subject, the composition comprising an active component comprising:
   from 0.1 to 5% by dry weight of an extract of *Allium*;
   from 0.1 to 5% by dry weight of an extract of Citrus;
   from 0.05 to 2.5% by dry weight of an extract of Paullinia; and
   from 0.05 to 2.5% by dry weight of an extract of *Theobroma*, wherein each % by dry weight is based on the total weight of the composition, and wherein the composition repigments the subject's hair back to its natural and original color.

2. The method according to claim 1, wherein the extract of *Allium* is an aqueous alcoholic extract of *Allium*, the extract of Citrus an aqueous alcoholic extract of Citrus, the extract of Paullinia is an aqueous alcoholic extract of Paullinia, and the extract of *Theobroma* is an aqueous alcoholic extract of *Theobroma*.

3. The method according to claim 1, wherein the extract of *Allium* is an extract of *Allium cepa*, the extract of the Citrus is an extract of Citrus lemon, the extract of the Paullinia is an extract of Paullinia cupana, and the extract of the *Theobroma* is an extract of *Theobroma cacao*.

4. The method according to claim 1, wherein the combined concentration of the extract of *Allium*, the extract of Citrus, the extract of Paullinia and the extract of *Theobroma* in the composition is from 1 to 30% dry weight based upon the volume of the composition.

5. The method according to claim 1, wherein the composition prevents and/or reduces further depigmentation of the hair.

6. The method according to claim 1, wherein the white or grey hair grows in as its natural and original color.

7. The method according to claim 1, wherein the active component consists of the extract of *Allium*, the extract of Citrus, the extract of Paullinia, and the extract of *Theobroma*, and wherein the composition further comprises an additive, an excipient, a carrier, or a combination thereof.

8. The method according to claim 7, wherein the active component consists of:
   from 0.3 to 2.35% by dry weight of the extract of *Allium*;
   from 0.1 to 0.2% by dry weight of the extract of Citrus
   from 0.05 to 0.1% by dry weight of the extract of Paullinia; and
   from 0.05 to 0.1% by dry weight of the extract of *Theobroma*.

9. A method for improving, increasing, stimulating, promoting and/or inducing the pigmentation of hair of a subject in need thereof, wherein said subject has white or grey hair, the method comprising: administering an effective amount of a composition to said subject, the composition comprising an active component comprising:

from 0.3 to 2.35% by dry weight of an extract of *Allium;*
from 0.1 to 0.2% by dry weight of an extract of Citrus
from 0.05 to 0.1% by dry weight of an extract of Paullinia; and
from 0.05 to 0.1% by dry weight of an extract of *Theobroma*, wherein each % by dry weight is based on the total weight of the composition, and wherein the composition repigments the subject's hair back to its natural and original color.

* * * * *